United States Patent [19]

Carduck et al.

[11] Patent Number: 5,554,741

[45] Date of Patent: Sep. 10, 1996

[54] PROCESS FOR THE PRODUCTION OF ALKYL AND/OR ALKENYL OLIGOGLUCOSIDES

[75] Inventors: Franz-Josef Carduck, Haan; Paul Schulz, Wuppertal; Rainer Eskuchen, Langenfeld, all of Germany

[73] Assignee: Henkel Kommanditgesellschaft auf Aktien, Duesseldorf, Germany

[21] Appl. No.: 295,757

[22] PCT Filed: Feb. 26, 1993

[86] PCT No.: PCT/EP93/00444

§ 371 Date: Sep. 1, 1994

§ 102(e) Date: Sep. 1, 1994

[87] PCT Pub. No.: WO93/18046

PCT Pub. Date: Sep. 16, 1993

[30] Foreign Application Priority Data

Mar. 6, 1992 [DE] Germany .................. 42 07 101.1

[51] Int. Cl.⁶ .................. C07H 1/00; C07H 3/04; C07H 3/06

[52] U.S. Cl. .................. 536/18.6; 536/4.1

[58] Field of Search .................. 536/18.6, 4.1

[56] References Cited

U.S. PATENT DOCUMENTS 2,390,507   12/1945   Cantor .................. 260/210

FOREIGN PATENT DOCUMENTS 0319616   6/1989   European Pat. Off. .
0362671   12/1990  European Pat. Off. .
9003977   4/1990   WIPO .

*Primary Examiner*—Gary L. Kunz
*Attorney, Agent, or Firm*—Wayne C. Jaeschke; John E. Drach; Henry E Millson, Jr.

[57] ABSTRACT

The aliphatic primary alcohols are reacted with a glycose, more especially glucose, in the presence of an acidic catalyst in certain process steps so that particularly light-colored and alkali-stable alkyl glucosides are obtained after a subsequent, compulsory bleaching step, which represents an improvement over known direct synthesis processes. The process may be carried out both on a laboratory scale and also on an industrial production scale.

16 Claims, No Drawings

PROCESS FOR THE PRODUCTION OF ALKYL AND/OR ALKENYL OLIGOGLUCOSIDES

BACKGROUND OF THE INVENTION

1. Field of the Invention

This invention relates to a process for the production of alkyl and/or alkenyl oligoglucosides by drying of an aqueous glucose/fatty alcohol suspension and subsequent acetalization of the dried mixture in the presence of acidic catalysts.

2. Statement of Related Art

Alkyl oligoglycosides are important nonionic surfactants for a number of applications. They are generally produced by acetalization of aldoses (mainly glucose) with fatty alcohols in the presence of acidic catalysts (direct process). However, to obtain high yields in sufficiently short reaction times, it is of advantage to carry out the reaction in the absence of water. More specifically, this means that only water-free starting materials, i.e. starting materials with a residual water content of not more than 2% by weight, may be used for the acetalization. International patent application WO 90/3977 is cited as representative of the extensive literature available on this subject.

The use of pure materials, for example pure water-free glucose, adds to the costs involved in the production of alkyl oligoglucosides to such an extent that economic production is often impossible. Accordingly, there has been no shortage of attempts in the past to use technical glucose based on inexpensive water-containing glucose sirups which have been dried to the necessary extent [EP-A1 0 319 616]. However, a major disadvantage in this connection was found to be that conventional drying processes always influence the quality and composition of the water-free products and, in particular, can contribute towards an unwanted increase in the content of oligosugars and polysugars.

Accordingly, the problem addressed by the present invention was to provide a new process for the production of alkyl and/or alkenyl oligoglucosides which would be free from the disadvantages mentioned above.

DESCRIPTION OF THE INVENTION

The present invention relates to a process for the production of alkyl and/or alkenyl oligoglucosides, characterized in that a) aqueous glucose sirups and fatty alcohols are dried in a turbo dryer with rotating fittings to a residual water content of 0.05 to 0.3% by weight and b) the resulting glucose/fatty alcohol suspensions are acetalized in known manner in the presence of acidic catalysts.

It has surprisingly been found that the drying of mixtures of water-containing glucose sirups with fatty alcohols in a turbo dryer gives water-free suspensions in which the content of oligosugars and polysugars is not unfavorably increased in relation to the starting material.

Glucose sirups are understood to be refined aqueous solutions of D-glucose, maltose and higher polymers of glucose (oligosaccharides, dextrins) which are obtained by acidic hydrolysis or enzymatic degradation of starch. The glucose sirups preferably used have a solids content of 50 to 85 and preferably 75 to 80% by weight and a DP1 degree (monomeric glucose content) of 80 to 99 and preferably 92 to 97% by weight, based on the solids.

Suitable fatty alcohols are primary alcohols corresponding to formula (I):

$$R^1OH \qquad (I)$$

in which $R^1$ represents linear or branched alkyl and/or alkenyl radicals containing 6 to 22 carbon atoms. Typical examples are caproic alcohol, caprylic alcohol, capric alcohol, lauryl alcohol, myristyl alcohol, cetyl alcohol, palmitoleyl alcohol, stearyl alcohol, oleyl alcohol, elaidyl alcohol, petroselinyl alcohol, arachyl alcohol, gadoleyl alcohol, behenyl alcohol and/or erucyl alcohol and technical cuts which may contain these alcohols in various mixing ratios. A technical fatty alcohol cut based on hydrogenated coconut oil containing 12 to 18 and, more particularly, 12 to 14 carbon atoms is preferred.

The molar ratio of glucose sirup to fatty alcohol may be 1:2 to 1:10 and is preferably 1:3 to 1:6, the ratio being based on the glucose in the sirup.

Turbo dryers in the context of the invention are cylindrical dryers, preferably of horizontal construction, in which rotating fittings turning at high speed provide for fine distribution of the material to be dried. In one preferred embodiment, the fittings in question are, for example, vanes, blades or paddles which are mounted on a rotating shaft (peripheral speed 5 to 25 and preferably 10 to 20 m/s). The actual drying process takes place at wall temperatures of 100° to 180° C. and at gas-phase temperatures of 150° to 220° C., preferably in the presence of air, inert gases, such as for example nitrogen or superheated steam, heat transfer taking place by convection and through the heated wall of the dryer. A temperature of 120° to 180° C. and a reduced pressure of 20 to 300 mbar and preferably 50 to 100 mbar have proved to be optimal for the production of water-free glucose/fatty alcohol suspensions.

Since the heated air or the heated inert gas are introduced into the dryer at the same time as the moist product to be dried, the water is instantaneously evaporated. By virtue of the high heat of evaporation of water, this leads to a temperature-stabilizing effect so that the drying process may even be carried out at high temperatures without any decomposition of temperature-labile products.

Accordingly, particular features of the turbo dryers to be used in accordance with the invention are the short residence time, the narrow residence time spectrum and the high temperature stabilization which provide for moderate treatment of the material to be dried, particularly in regard to composition and color.

The dry material may be separated from the gas phase, for example in a vacuum separation vessel. To minimize product losses, it is also advisable to pass the waste gas through a heated column for example, to condense entrained fatty alcohol and to return it to the suspension.

The water-free glucose/fatty alcohol suspensions obtainable by the process according to the invention have a residual water content of 0.1 to 2% by weight. They may be acetalized in known manner in the presence of acidic catalysts, for example p-toluenesulfonic acid, to form the corresponding alkyl and/or alkenyl oligoglucosides.

The following Examples are intended to illustrate the invention without limiting it in any way.

EXAMPLES

A) Preparation of an Anhydrous Glucose/fatty Alcohol Suspension

The suspension was prepared in a horizontally arranged turbo dryer (type ES 2050 manufactured by the Vomm company of Milan, Italy; turbine diameter 340 mm, turbine length 2.4 m) in which a shaft fitted with vanes or blades rotated at high speed.

Starting Materials:

A1) Glucose sirup

Solids content: 75% by weight

DP1 content(*): 95% by weight (*) Monomeric glucose content, based on solids a2) $C_{12/14}$ Coconut oil fatty alcohol (Lorol® Spezial, a product of Henkel KGaA, Düsseldorf).

The starting materials were separately preheated to a temperature of 60° C. First, the fatty alcohol was pumped into the "head" of the turbo mixer by a piston pump. The glucose sirup was then introduced at some distance (looking along the longitudinal axis of the dryer) by a second piston pump. The molar ratio of glucose sirup to fatty alcohol was 1:4.5, based on the glucose in the sirup. At a rotational speed of 1,000 r.p.m., the mixture was finely dispersed in a hot, turbulent airstream and at the same time freed from water.

The drying temperature was in the range from 160° to 180° C. and was transferred on the one hand by convection and on the other hand through the heated wall of the dryer. A pressure of 100 mbar was established at the mixer exit.

The glucose/fatty alcohol slurry was discharged into a vacuum separation vessel at the mixer exit and the gas phase—containing steam and entrained fatty alcohol—was passed through a heated column and through a heated heat exchanger. The fatty alcohol was condensed and returned while the steam was precipitated in a following condenser.

The resulting glucose/fatty alcohol suspension had a residual water content of 0.1% by weight.

B. Acetalization 1,050 g of the water-free glucose/fatty alcohol suspension from A) were introduced into a 2-liter three-necked flask equipped with a stirrer, distillation column and internal thermometer and heated to 110° C. under a reduced pressure of around 20 mbar.

0.1 to 0.5% by weight, based on the glucose, of p-toluenesulfonic acid in the form of a 5% by weight solution in coconut oil fatty alcohol was then added to the reaction mixture. To displace the equilibrium, the water of reaction was continuously distilled off and the reaction was terminated after the separation of water had stopped and the residual content of unreacted glucose in the mixture was less than 0.1% by weight, based on the starting quantity. The reaction mixture was then neutralized with magnesium oxide and the excess coconut oil fatty alcohol was removed under reduced pressure (approx. 1 mbar) and at a temperature of 180° C. by means of a thin-layer evaporator.

What is claimed is:

1. A process for producing an alkyl or alkenyl oligoglucoside or mixture thereof comprising the steps of: (1) providing a mixture comprised of an aqueous syrup of glucose and at least one fatty alcohol containing from 6 to 22 carbon atoms; (2) forming a water-free suspension by drying said mixture to a residual water content of from about 0.05 to about 0.3% in a turbo dryer having rotating fittings therein; (3) forming an alkyl or alkenyl oligoglucoside or mixture thereof by reacting said water-free suspension in the presence of an acid catalyst.

2. The process of claim 1 wherein said aqueous syrup has a solids content of from about 50% to about 85% by weight.

3. The process of claim 2 wherein from about 80% to about 99% of said solids is glucose having a DP equal to 1.

4. The process of claim 1 wherein said at least one fatty alcohol is at least one compound of the formula (I):

$$R^1OH \qquad (I)$$

wherein $R^1$ contains from 12 to 18 carbon atoms and is selected from the group consisting of linear alkyl, branched alkyl, linear alkenyl, and branched alkenyl.

5. The process of claim 1 wherein the molar ratio of glucose to fatty alcohol in said mixture is from about 1:2 to about 1:10.

6. The process of claim 5 wherein said molar ratio of glucose to fatty alcohol in said mixture is from about 1:3 to about 1:6.

7. The process of claim 1 wherein step (2) is carried out at a temperature of from about 120° C. to about 200° C.

8. The process of claim 1 wherein step (2) is carried out in the presence of air, inert gas, superheated steam, or a combination thereof.

9. The process of claim 1 wherein the aqueous syrup of glucose is a refined aqueous solution of D-glucose, maltose, and higher polymers of glucose.

10. The process of claim 2 wherein said aqueous syrup has a solids content of from about 75% to about 80% by weight.

11. The process of claim 3 wherein from about 92% to about 97% of said solids is glucose having a DP equal to 1.

12. The process of claim 7 wherein step (2) is carried out at a temperature of from about 120° to about 180° C. and at a reduced pressure of from about 20 to about 300 mbar.

13. The process of claim 12 wherein said reduced pressure is from about 50 to about 100 mbar.

14. The process of claim 1 wherein the product from step (3) has a residual water content of from about 0.1% to about 2% by weight.

15. The process of claim 1 wherein in step (1) said at least one fatty alcohol is at least one compound of the formula:

$$R^1OH \qquad (I)$$

wherein $R^1$ is selected from the group consisting of linear alkyl, branched alkyl, linear alkenyl, and branched alkenyl; the aqueous syrup has a solids content of from about 50% to about 85% by weight; the molar ratio of glucose to fatty alcohol in said mixture is from about 1:2 to about 1:10; and step (2) is carried out at a temperature of from about 120° to about 180° C. and at a reduced pressure of from about 20 to 300 mbar.

16. The process of claim 15 wherein in step (1) the aqueous syrup has a solids content of from about 75% to about 80% by weight and from about 92% to about 97% of said solids is glucose having a DP equal to 1; said molar ratio of glucose to fatty alcohol in said mixture is from about 1:3 to about 1:6; and step (2) is carried out at a reduced pressure of from about 50 to about 100 mbar in the presence of air, inert gas, superheated steam, or a combination thereof.

* * * * *